United States Patent [19]

Shimasue

[11] Patent Number: 5,340,850

[45] Date of Patent: Aug. 23, 1994

[54] COMPOSITE RESIN FOR USE IN DENTISTRY AND METHOD FOR TREATING SAME TO PROVIDE ANTIMICROBIAL AND MICROBICIDAL PROPERTIES

[75] Inventor: Yoshiyuki Shimasue, Osaka, Japan

[73] Assignee: Elsol Products Corporation, Tokyo, Japan

[21] Appl. No.: 21,370

[22] Filed: Feb. 23, 1993

[51] Int. Cl.$^5$ .................. A61F 2/00; B05D 3/06
[52] U.S. Cl. ...................... 523/115; 523/113; 523/116; 524/403; 427/523; 427/529
[58] Field of Search ........... 523/115, 116; 524/403; 427/523, 529

[56] References Cited

U.S. PATENT DOCUMENTS 4,718,905  1/1988  Freeman .................... 623/6
4,849,223  7/1989  Pratt et al. ................ 523/116

*Primary Examiner*—Paul R. Michl
*Assistant Examiner*—LaVonda R. DeWitt
*Attorney, Agent, or Firm*—Jordan and Hamburg

[57] ABSTRACT

A composite resin for use in dentistry contains a synthetic resin and an inorganic filler, in various forms such as a filling material for restoring carious tooth cavities or decayed teeth in the mouth, a bonding agent for dental crowns and bridges, a dental cement, or any other adhesive. Active elements of either ions or radicals having antimicrobial and microbicidal properties are implanted into at least one of the synthetic resin and the inorganic filler. A method for preparing such a composite resin is also provided.

4 Claims, 1 Drawing Sheet

COMPOSITE RESIN FOR USE IN DENTISTRY AND METHOD FOR TREATING SAME TO PROVIDE ANTIMICROBIAL AND MICROBICIDAL PROPERTIES

BACKGROUND OF THE INVENTION

This invention relates to a composite resin for use in dentistry, and a method for treating same to impart antimicrobial and microbicidal properties thereto. More particularly, the present invention relates to a composite resin adapted for application to carious tooth cavities and decayed portions of teeth in the mouth, in various forms such as a filling material for restoring teeth, a bonding agent for dental crowns and bridges, a dental cement, or any other adhesive.

In the following description, the term "active element" is used to refer to an ion or a radical.

A composite resin, in a form such as a filling material for tooth restoration, a bonding agent, an adhesive or the like, generally contains a rigid synthetic resin and an inorganic filler. In application thereof, at first the composite resin is filled in the portions in the mouth to be treated, and then hardened and bonded by means of a photochemical polymerization reaction using ultraviolet rays, or other chemical reaction.

However, a composite resin of this type tends to corrode in the portions contacting the tooth and peel away from the surfaces of the tooth enamel or dentine, due to the attack of cariogenic bacteria and the like after use for an extended period. The mechanical strength of such composite resins per se may also be reduced.

In addition, the color of the tooth may deteriorate due to the accretion and corrosion of food remnants left on the tooth.

SUMMARY OF THE INVENTION

Accordingly, it is a major object of the present invention to provide a composite resin and a method for preparation thereof, which can prevent corrosion in the portions contacting the tooth, the subsequent separation of the composite resin from the tooth, and the deterioration of the color of the tooth, while maintaining excellent mechanical strength such as wear resistibility.

To achieve the above object, there is provided a composite resin for use in dentistry containing a synthetic resin and an inorganic filler, wherein active elements having antimicrobial and microbicidal properties are implanted into at least one of the synthetic resin and the inorganic filler.

There is further provided a method for treating the composite resin for use in dentistry to impart antimicrobial and microbicidal properties thereto, the method including implanting active elements having antimicrobial and microbicidal properties into at least one of the synthetic resin and the inorganic filler.

Thus, the composite resin of the present invention can prevent the propagation of bacteria therein and the corrosion occurring between the composite resin and the tooth, resulting in long and comfortable application to the tooth in the mouth without any trouble such as the separation of the composite resin from the tooth.

BRIEF DESCRIPTION OF THE DRAWING

The present invention will be more fully understood from the detailed description given hereinbelow read in conjunction with the accompanying drawings, which are given by way of illustration only, and thus are not limitative of the present invention, and wherein.

DESCRIPTION OF THE PREFERRED EMBODIMENT

A composite resin is prepared from a rigid synthetic resin and silicon dioxide ($SiO_2$), as an example of an inorganic filler, into which silver ions are implanted.

The method for treating the composite resin containing the rigid synthetic resin and silicon dioxide ($SiO_2$) to impart antimicrobial and microbicidal properties thereto by ion implantation will be discussed below.

Figure 1:
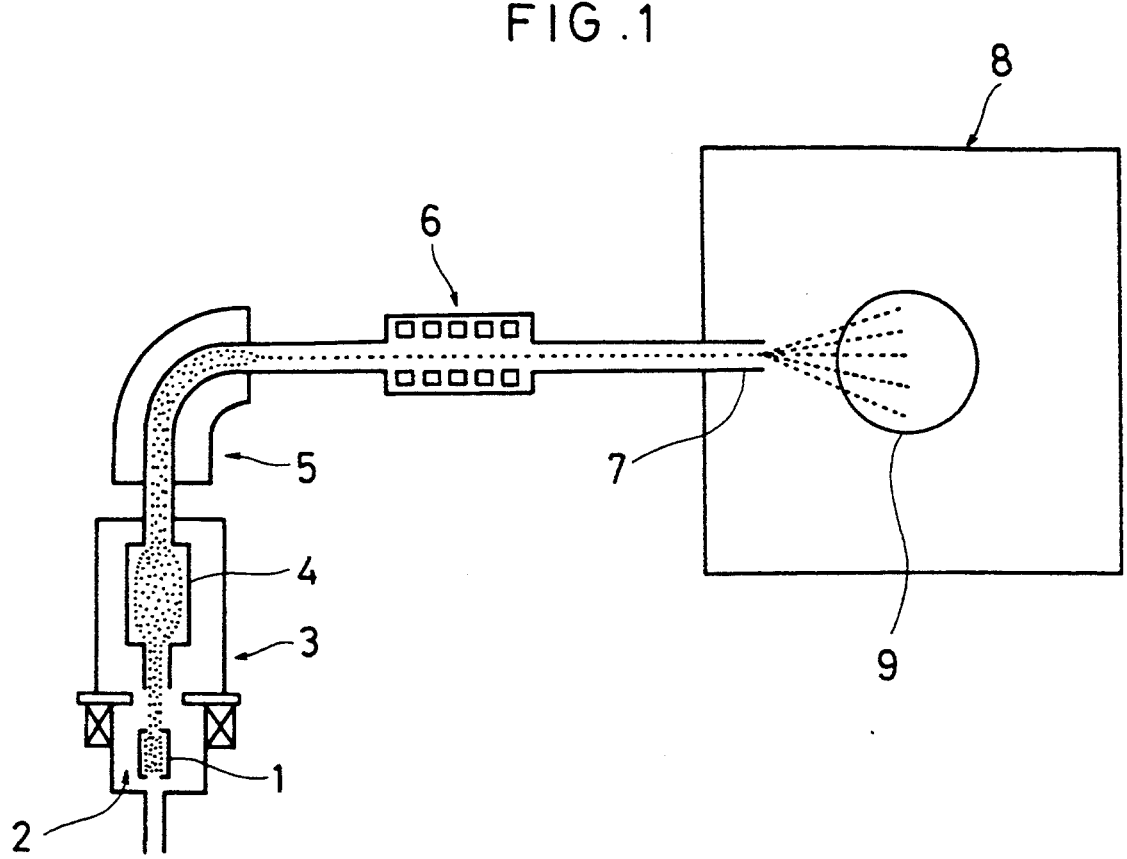
FIG. 1 is a schematic plan view illustrating an ion implantation apparatus of the present invention for implanting silver ions into an inorganic filler.

Referring now to FIG. 1, an ion implantation apparatus comprises a gas oven 1 for generating gas, an ion forming unit 2 for forming ions, an electrode 3 for extracting the ions from the ion forming unit 2, an electrode assembly 4 for collecting the extracted ions to form highly concentrated ions and accelerating the ions at high velocity, a mass separating unit 5 for selectively extracting preferable silver ions, an electrode assembly 6 for accelerating the extracted silver ions based upon predetermined energy levels, and a chamber 8 for storing inorganic filler (not shown), into which silver ions are implanted.

In the operation of the ion implantation apparatus, the ion implantation apparatus of the above structure is maintained at high vacuum with a vacuum pump (not shown). The heating oven 1 heats silver to form gaseous silver. The gaseous silver is supplied to the ion forming unit 2. The ions formed in the ion forming unit 2 are selectively extracted with the electrode 3. The electrode assembly 4 collects the ions to form highly concentrated ions and leads the ions to the mass separating unit 5 where preferable silver ions are selectively extracted. The extracted silver ions are then accelerated with the electrode assembly 6 and led to the chamber 8 containing the inorganic filler. The silver ions are directed to the inorganic filler placed in the chamber 8 through a port 7 such that the silver ions are implanted into the inorganic filler.

Figure 2:
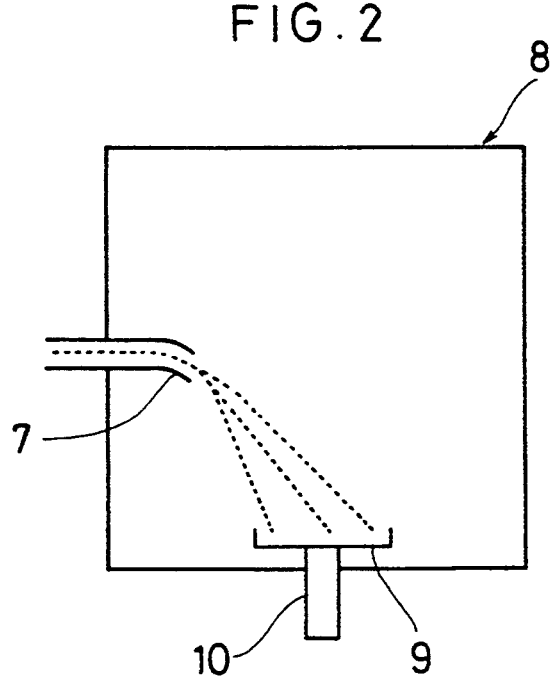
FIG. 2 is a side view of the apparatus shown in FIG. 1.

Referring now to FIG. 2, the inorganic filler is placed on a plate 9 which is rotatably supported by a support 10 such that substantially all surfaces of the inorganic filler can be subjected to ion implantation.

After the completion of the above process, the silver ion implanted inorganic filler is mixed with the rigid synthetic resin to prepare a composite resin for use in dentistry.

Antimicrobial Activity Test

Testing conducted under various conditions, in order to determine the antimicrobial activity of the silver ion-implanted inorganic filler made as described above, will be discussed below.

Test Method

Silver ions at a concentration of 100 ppm are implanted into 0.1 grams and 0.5 grams of inorganic filler, respectively. These two silver ion-implanted fillers and a control filler not subjected to ion implantation are mixed, respectively, with 1 milliliter of a liquid culture medium containing carious tooth bacteria. These three samples are maintained at 37° C. for predetermined periods: two hours, six hours and twelve hours, respectively. 0.1 milliliters of each sample are removed at the end of each predetermined time period and diluted at a predetermined rate. Each of the diluted samples is then cultured in nutrient agar for determining the number of colonies generated therein. The actual number of the generated colonies in the liquid culture medium is determined by multiplying the number of colonies generated in the nutrient agar by the rate of the dilution.

Test Result

The following are the tabulated test results:

TABLE 1

| Test bacteria | Elapsed times (hours) | Non-treated Control | Actual Number of Colonies Silver ion-implanted filler at 100 ppm concentration | |
|---|---|---|---|---|
| | | | 0.1 grams inorganic filler | 0.5 grams inorganic filler |
| S. mutans ATCC 148 | 2 | $4.0 \times 10^5$ | $4.0 \times 10^4$ | $5.3 \times 10^3$ |
| | 6 | $2.0 \times 10^5$ | $2.0 \times 10^3$ | 0 |
| | 12 | $1.4 \times 10^5$ | 0 | 0 |
| S. mitior 0955 | 2 | $8.0 \times 10^4$ | $3.6 \times 10^3$ | $6.0 \times 10^3$ |
| | 6 | $5.4 \times 10^4$ | 0 | 0 |
| | 12 | $5.5 \times 10^4$ | 0 | 0 |

It is apparent from TABLE 1 that the composite resin containing silver ion-implanted filler results in a lower number of residual carious tooth bacteria as compared with the Control, under all conditions, which accordingly demonstrates excellent antimicrobial activity against carious tooth bacteria.

In the above embodiment, silicon dioxide is used as an example of the inorganic filler. However, it will be obvious to one skilled in the art that various materials such as silica, quartz, silicon nitride and zinc oxide can be used as the inorganic filler. In fact, any inorganic filler used in conventional composite resins for use in dentistry is suitable for use as the inorganic filler in the present invention.

In addition, the method for implanting active elements and the arrangement of the active element implantation apparatus are not limited to the above-described embodiment.

Furthermore, the active element is not limited to ions. Radicals can be implanted into the inorganic filler or synthetic resin. Suitable ions are not limited to silver ions. Metal ions of platinum, copper, zinc and the like can be substituted in place of silver ions. Ions other than metal ions can also be used. Ion implantation conditions, and the number of ions to be implanted, are not limited to those employed in the above embodiment.

In the above embodiment, the ions are implanted into the inorganic filler, and the ion-implanted inorganic filler is mixed with the synthetic resin. However, the active elements i.e., the ions or radicals, can be implanted into a mixture of the synthetic resin and the inorganic filler. In this regard, the active elements may be implanted into both the synthetic resin and the inorganic filler. It is also possible to implant the active elements only into the synthetic resin. However, it is essential that the active elements i.e., ions or radicals having antimicrobial and microbicidal properties, are implanted into at least one of the synthetic resin and the inorganic filler.

A composite resin in the various forms of a filling material for restoring carious tooth cavities, a bonding agent for dental crowns and bridges, a dental cement and the like, are contemplated within the scope of the present invention.

This specification is by no means intended to restrict the present invention to the preferred embodiments set forth therein. Various modifications to the invented composite resin and method for treating a composite resin, as described herein, may be made by those skilled in the art without departing from the spirit and scope of the present invention.

What is claimed is:

1. A composite resin for use in dentistry, comprising a synthetic resin; an inorganic filler; and ions having antimicrobial and microbicidal properties implanted into at lest one of said synthetic resin and said inorganic filler 2. The composite resin of claim 1, wherein said ions are silver ions.

3. A method for treating a composite resin for use in dentistry to impart antimicrobial and microbicidal properties thereto, comprising implanting ions having antimicrobial and microbicidal properties into at least one of a synthetic resin and an inorganic filler.

4. The method of claim 3, wherein said ions are silver ions.

* * * * *